US 6,687,000 B1

(12) United States Patent
White

(10) Patent No.: US 6,687,000 B1
(45) Date of Patent: Feb. 3, 2004

(54) PHOTON-SORTING SPECTROSCOPIC MICROSCOPE SYSTEM

(75) Inventor: John G. White, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 544 days.

(21) Appl. No.: 09/603,687

(22) Filed: Jun. 26, 2000

(51) Int. Cl.[7] .............................. G01J 3/28; G01J 3/00
(52) U.S. Cl. ...................... 356/328; 356/300
(58) Field of Search ........................ 356/318, 300, 356/319, 311, 320, 328, 326

(56) References Cited

U.S. PATENT DOCUMENTS

| | | |
|---|---|---|
| 3,541,542 A | 11/1970 | Duguay et al. |
| 4,349,907 A | 9/1982 | Campillo et al. |
| 5,032,720 A | 7/1991 | White |
| 5,034,613 A | 7/1991 | Denk et al. |
| 5,035,476 A | 7/1991 | Ellis et al. |
| 5,260,578 A | 11/1993 | Bliton et al. |
| 5,289,407 A | 2/1994 | Strickler et al. |
| 5,296,700 A | 3/1994 | Kumagai |
| 5,296,703 A | 3/1994 | Tsien |
| 5,303,165 A * | 4/1994 | Ganz et al. .............. 356/319 |
| 5,377,003 A | 12/1994 | Lewis et al. |
| 5,386,112 A | 1/1995 | Dixon |
| 5,523,573 A | 6/1996 | Hanninen et al. |
| 5,583,342 A | 12/1996 | Ichie |
| 5,777,732 A | 7/1998 | Hanninen et al. |
| 5,781,289 A * | 7/1998 | Sabsabi et al. ............. 356/318 |
| 5,796,112 A | 8/1998 | Ichie |
| 6,138,082 A * | 10/2000 | Wang et al. ............... 702/109 |
| 6,249,341 B1 * | 6/2001 | Basiji et al. ............... 356/73 |

FOREIGN PATENT DOCUMENTS

| FR | 2532756 | 3/1984 |
|---|---|---|
| JP | 61-138146 | 6/1984 |
| WO | WO 97/11355 | 3/1997 |
| WO | WO 99/37999 | 7/1999 |

OTHER PUBLICATIONS

Lisa A. Kelly, et al., "Time–Resolved Fluorescence Polarization Measurements for Entire Emission Spectra with a Resistive–Anode, Single–Photon–Counting Detector: The Fluorescence Omnilyzer," Rev. Sci. Instrum., vol. 68, No. 6, Jun., 1997, pp. 2279–2286.

Winfried Denk, et al., "Two–Photon Laser Scanning Fluorescence Microscopy," Science, vol. 248, Apr. 6, 1990, pp. 73–76.

(List continued on next page.)

Primary Examiner—Russell Adams
Assistant Examiner—D. Ben Esplin
(74) Attorney, Agent, or Firm—Foley & Lardner

(57) ABSTRACT

A photon sorting spectroscopic microscope system focuses light from an excitation source onto a specimen through a microscope objective lens to excite fluorescence in the specimen. The fluorescent light is passed back through the objective on a beam path and is directed by a dichroic mirror on a second beam path to a spectral dispersive element which spreads the light according to its spectral content. A multi-channel detector with multiple detector elements receives the light spread by the spectral dispersive element and provides output signals indicative of photon events. The photon events in each channel may be counted to provide the spectral content of the fluorescent signal as the excitation beam is scanned in a raster fashion over the sample. Two dimensional fluorescence lifetime analysis may further be provided by utilizing multiple counters on each channel which are sequentially enabled after a pulse of light from the source, providing photon counts in each spectral channel as a function of time delay from the excitation light pulse.

35 Claims, 6 Drawing Sheets

OTHER PUBLICATIONS

Winfried Denk, et al., "Two–Photon Molecular Excitation in Laser Scanning Microscopy," Handbook of Biological Confocal Microscopy, Phenum Press, New York, 1995, Chapter 28, pp. 445–458.

David L. Wokosin, et al., "All–Solid–State Ultrafast Lasers Facilitate Multi–Photon Excitation Fluorescence Imaging," IEEE J. of Selected Topics in Quantum Electronics, vol. 2, No. 4, Dec. 1996, pp. 1051–1065.

Lisa A. Kelly, et al., "Time–Resolved Fluorescence Polarization Measurements for Entire Emission Spectra With a Resistive–Annode, Single–Photon–Counting Detector: The Fluorescence Omnilyzer," Rev. Sci. Instrum. vol. 68, No. 6, Jun. 1997, pp. 2279–2286.

Spencer D. Pack et al., "Photon–Counting Technique For Rapid Fluorescence–Decay Measurement," Opt. Letters, vol. 23, No. 15, Aug. 1, 1998, pp. 1215–1217.

David L. Wokosin, et al., "Detection Sensitivity Enhancements For Fluorescence Imaging With Multi–Photon Excitation Microscopy," Proc. 20$^{th}$ Ann. Int. Conf. of the IEEE Eng. In Med. and Biology Society, vol. 20, No. 4, 1998, pp. 1707–1714.

Joseph R. Lakowicz, *Principles of Fluorescence Spectroscopy*, 2d. Ed., Kluwer Academic/Plenum Publishers, NY, 1999 (book), pp. 25–60, 95–118.

* cited by examiner

PHOTON-SORTING SPECTROSCOPIC MICROSCOPE SYSTEM

This invention was made with United States Government support warded by the following agencies: NIH RR00570. The United States Government has certain rights in this invention.

FIELD OF THE INVENTION

This invention pertains generally to the field of microscopy and spectroscopy, and particularly to laser scanning fluorescence microscopy.

BACKGROUND OF THE INVENTION

Scanning optical microscopes, such as laser scanning confocal microscopes, are of increasing importance in microscopy, particularly for imaging of dynamic biological structures such as living cells. In a scanning microscope, the light beam from the source, usually a laser, is focussed to a point within the specimen by the microscope objective and the specimen and beam are moved relative to one another in a raster fashion, either by moving the stage on which the specimen is mounted or, more commonly, by deflecting the light beam so that it scans across a stationary specimen. The light from the specimen is collected by the objective and passed back through the microscope to a detector, such as a photomultiplier tube. In addition to detection of light reflected from a specimen (or transmitted through the specimen), scanning microscopes can also be constructed to detect fluorescence induced by the illuminating light beam. Typically, the fluorophores in the specimen absorb the illumination light, which is at a chosen wavelength (usually shorter wavelength visible light), and fluorescently emit photons at a longer wavelength which are received by the objective of the microscope and passed back through the scanning optics to a dichroic mirror which separates the fluorescent light from light at the illuminating light wavelengths and directs the fluorescent light to a separate photodetector. In this manner, particular structures within the specimen, such as parts of cells, can be labeled with fluorescent markers and distinctively imaged by the scanning microscope.

Most fluorophores can also absorb two (or more) photons of longer wavelengths simultaneously when sufficiently intense illumination light is applied thereto and will emit a fluorescent photon at a shorter wavelength than the incident light. This phenomenon is exploited in multi-photon laser scanning microscopes in which an incident beam of relatively long wavelength light in short pulses from a laser source is narrowly focussed onto a specimen so that the light reaches an intensity at the focal point sufficient to excite detectable two (or more) photon fluorescence. The emitted fluorescent photons collected by the objective lens of the microscope are passed back through the optical system, either through the scanning optics to a dichroic mirror which reflects light at longer wavelengths while passing the shorter wavelength fluorescent light to a separate detector, or by bypassing the scanning system, and directing the light from the microscope objective lens to a dichroic mirror which passes the shorter wavelength fluorescent light directly to a detector while reflecting the longer wavelength excitation light. See, Winfried Denk, et al., "Two Photon Laser Scanning Fluorescence Microscopy," Science, Vol. 248, Apr. 6, 1990, pp. 73–76; Winfried Denk, et al., "Two-Photon Molecular Excitation in Laser-Scanning Microscopy," Chapter 28, Handbook of Biological Confocal Microscopy, Plenum Press, New York, 1995, pp. 445–458; and U.S. Pat. No. 5,034,613 entitled Two-Photon Laser Microscopy. By focussing the incident light from the objective lens to a relatively narrow spot or beam waist such that the intensity of the incident light is sufficient to excite multi-photon excitation only at the waist within the specimen, multi-photon fluorescence excitation will occur generally only in the focal plane. The shorter wavelength fluorescent light emitted by the specimen can then be passed back, either through the scanning system to de-scan the light or directly, without de-scanning, to a fluorescent light detector to obtain an image corresponding to the focal plane. Therefore, the excitation light alone produces the desired depth resolution (i.e., an optically sectioned fluorescence image), so that there is no need for the use of a confocal aperture.

Fluorescent signal photons can be characterized by their wavelength, the lifetime of the excited state giving rise to the photon, and polarization. These parameters can be used to identify a fluorophore or to provide information on the microenvironment of the fluorophore. Fluorescence microscopy of living specimens generally yields very weak signals. Therefore, any multi-dimensional spectral imaging system must be very photon efficient to be practical for in vivo imaging. In addition, such systems must have the lowest possible values of intrinsic (i.e., system generated) noise. Living cell studies, such as four dimensional imaging or ion imaging, generally require faster imaging speeds than are currently available from commercial multi-photon laser scanning microscopes (MPLSM). Several fast scanning MPLSM systems are currently in use in research laboratories, but these instruments either do not preserve the deep section contrast advantages of multi-photon over confocal microscopy or do not allow use of electronic magnification of the scanned area.

Most biological tissue is autofluorescent. Molecules such as NAD(P)(H), elastin, and chlorophyll act as endogenous fluorophores. These endogenous fluorophores can often be identified by their characteristic spectra. A spectral imaging system would thus be of considerable use in identifying endogenous fluorophores and specifying spectral windows that would either maximally accept or reject these signals, depending on the application.

The use of engineered fluorescent probes as physiological indicators has become a well established technique. Some probes indicate the presence of a bound ligand by changes in fluorescence intensity (e.g., calcium Green 1) while others use spectral shifts (e.g., Indo 1). The latter are favored because ratio imaging at two different wavelengths may be used to provide measurements that are independent of the concentration of the indicator molecule, requiring quantitative measurements. However, each of these probes now requires the use of a custom two-channel filter set.

Fluorescence resonant energy transfer (FRET) is a powerful technique for measuring intermolecular distances in vivo. This technique also now requires custom filter sets that are matched to the donor and the acceptor molecule's emission spectra. Ratiometric measurements are used to measure the extent of resonance transfer. This technique is proving to be valuable for the in vivo visualization of the docking of a receptor with its ligand, and is the basis of operation of a GFP based calcium indicator.

Fluorescence in situ hybridization is another significant area where multiple fluorophores and ratiometric techniques are used. Often, the main requirement in this application is to spectrally resolve as many separate fluorescent probes as possible.

A major consideration in the detection of fluorescence from scanning microscopes is the ability to collect the desired signal in the presence of significant noise (detection noise, system noise, fluorescent background, etc.). Background fluorescence from endogenous fluorophores or from another interfering exogenous fluorophore can severely reduce detection, or interpretation, of the image signal. In samples labeled with multiple fluorophores, the signal from one fluorophore is often much stronger than another and can spill over to an adjacent channel. In such instances, it is often necessary to move the spectral detection windows as far apart as possible to aid discrimination between the two fluorophores being studied rather than choosing spectral windows to give the maximum signal in each channel. The use of multiple fluorescent labels has been commonplace in the study of fixed specimens, and is now being established for use in in vivo studies. There are now many fluorophores that are available, each with its own unique spectral characteristics. The large number of available fluorophores has carried with it the problem that many different filter sets are now required for double or triple labeled samples. Filter sets use expensive interference filters and dichroic mirrors, and are often difficult to interchange. An ideal filter would have to be continuously adjustable so that for any particular combination of fluorophores used, an optimal set of band-pass assignments could be selected for each detection channel to minimize signal bleed-through and maximize the signal-to-noise ratio.

There are several major advantages that a spectral imaging system would have over a conventional, filter-based three-channel detector. These include dynamic identification of auto-fluorescence and optimization of windows for rejection or imaging as required; dynamic optimization of spectral windows for multiple labels; dynamic background subtraction of reference spectra before the image is even displayed; identification of spectral shifts of fluorophores in different environments; full signal optimization for any ratiometric indicator; fluorophore separation after data collection if a full spectral image is taken can be carried out; and evaluation of standard histological procedures for MPLSM analysis is permitted for identification of tissue-specific spectral shifts of staining.

There are two types of spectral imaging systems currently available commercially. One type uses a Fourier transform spectrometer attached to a standard fluorescence microscope. These systems (an example of which is marketed by Applied Spectral Imaging) split the imaging path in a Sagnac interferometer. Successive interferograms are obtained as the optical path length of one arm of the spectrometer is scanned. Spectral information is recovered by reverse Fourier transformation of the captured stack of interferograms. This method can give high resolution spectral information at each pixel of an image, but has the disadvantage that many interferograms have to be collected, each requiring a separate image. Thus, many frames must be captured with a consequent high level of fluorophore exposure to excitation. In addition, the technique is computationally intensive and requires several minutes to collect data and to compute a spectrogram. Because spectral image reconstruction is so slow, the technique is only suitable for fixed specimens. A further limitation for 3D MPLSM systems is that well collimated light is needed for the interferometer. Scattered emission light that could normally be used for MPLSM imaging cannot be used with this type of imaging spectrometer. A second type of spectral imaging system, available commercially from Leica (the Leica SP) is a confocal microscope that features adjustable spectral windows for signal detection. The system has four detection channels that can be assigned to four arbitrary, non-overlapping regions of the spectrum, and uses a simple prism spectrometer and a system of adjustable, reflecting slits to select parts of the spectrum to four photomultiplier tubes. Light impinging on the sides of one slit is deflected into an adjacent photomultiplier. This scheme is efficient but is limited to four channels, and is thus not a spectral imaging system as such. More channels would be required to visualize the shape of a spectrum so as to identify fluorophores (such as sources of background fluorescence) on the basis of their characteristic emission spectra. The prism spectrometer utilized in the Leica SP capitalizes on the highly collimated signal light path in a conventional confocal microscope. However, there are advantages in positioning the detectors in a MPLSM imaging system so that the maximum amount of scattered (non-collimated) light is also collected for signal detection. See Wokosin, et al., "Detection Sensitivity Enhancements for Fluorescence Imaging With Multi-Photon Excitation Spectroscopy," Proc. $20^{th}$ Int'l. Conf. IEEE Engr. In Medicine and Biology Soc., Vol. 20, No. 4, 1998. This scattered light collection technique cannot be utilized with a de-scanned emission prism spectrometer using high F-number optics, and thus a key advantage of MPLSM, enhanced emission collection and deeper imaging, would not be readily obtained with this type of spectrometer.

Time-resolved fluorescence spectroscopy is a well-established technique for studying the emission dynamics of fluorescent molecules, i.e., the distribution of times between the electronic excitation of a fluorophore and the radiative decay of the electron from the excited stated producing an emitted photon. The temporal extent of this distribution is referred to as the fluorescence lifetime of the molecule. Lifetime measurements can yield information on the molecular microenvironment of a fluorescent molecule. Factors such as ionic strength, hydrophobicity, oxygen concentration, binding to macromolecules and the proximity of molecules that can deplete the excited state by resonance energy transfer can all modify the lifetime of a fluorophore. Measurements of lifetimes can therefore be used as indicators of these parameters. Furthermore, these measurements are generally absolute, being independent of the concentration of the fluorophore. This can have considerable advantages. For example, the intracellular concentrations of a variety of ions can be measured in vivo by fluorescence lifetime techniques. Many popular, visible wavelength calcium indicators, such as Calcium Green, give changes of fluorescence intensity upon binding calcium. The intensity-based calibration of these indicators is difficult and prone to errors. However, many dyes, such as calcium crimson, exhibit useful lifetime changes on calcium binding and therefore can be used with lifetime measurements. This gives the considerable advantage that absolute measurements of concentration can be made with no elaborate calibration procedures required. Alternatively, lifetime measurements may be used to calibrate the intensity signals from these indicators when maximum sensitivity is required.

An exciting new development has been the technique of fluorescence lifetime imaging microscopy (FLIM). In this technique, lifetimes are measured at each pixel and displayed as contrast. Lifetime imaging systems have been demonstrated using wide-field, confocal and multi-photon imaging modes. FLIM combines the advantages of lifetime spectroscopy with fluorescence microscopy by revealing the spatial distribution of a fluorescent molecule together with information about its microenvironment. In this way, an extra dimension of information is obtained. This extra dimension can be used to discriminate among multiple labels on the basis of lifetime as well as spectra. This would allow more labels to be discriminated simultaneously than by spectra alone in applications where many labels are required, such as FISH, for example. There are also promising applications of lifetime imaging in the medical sciences. For example, tumors have been detected in mice sensitized with a hematoporphorin derivative by lifetime imaging.

Multi-photon lifetime imaging of live specimens is particularly interesting. In these applications, lifetime imaging in conjunction with spectral imaging, should greatly facilitate studies using ion indicator probes and FRET studies of intermolecular distances. Lifetime measurements are a sensitive indicator of FRET and, in combination with spectral measurements, should provide a more sensitive indication of, for example, calcium levels when used with FRET based calcium indicators such as cameleon.

Lifetime measurements are a means of providing another dimension of information from fluorescent probes used in vivo. In most applications where probes are viewed in four-dimensions in vivo, there is a benefit from more or better information. Fluorescent lifetimes can be measured either in the frequency domain or in the temporal domain. Three general strategies have been used to measure fluorescence lifetimes.

A first technique is frequency domain imaging in which a high-frequency, modulated light source is used for fluorophore excitation. By the use of a gain-modulated detector, the phase shift and amplitude demodulation of the fluorescence signal is determined. From these data, the fluorescent lifetime of the probe can be calculated. This scheme is robust and has been extensively used. However, it suffers from several drawbacks: the detector is only working at 50% of its maximum efficiency because it is gain modulated, several data sets taken at different excitation modulation frequencies have to be taken in order to separate two or more lifetime components and, finally, this scheme does not work well with photon counting techniques.

A second technique is time-domain lifetime imaging with gated detector in which a gated micro-channel plate image intensifier is used in conjunction with a CCD imaging camera. Spectral information is obtained by gating the image intensifier on for a narrow time-window at progressively later intervals after the excitation pulse in a succession of data frame captures. This scheme is probably the simplest way of implementing a lifetime imaging system. However, it suffers from two major drawbacks. The method has very poor photon utilization as only one temporal interval is detected at a time. If there are 32 intervals, for example, $31/32$ of the signals is not utilized and 32 separate frames have to be captured. The second reason this scheme is not appropriate for a multi-photon imaging application is that an imaging (i.e., area) detector is used. This means that the deep sectioning advantage of multi-photon imaging is not realized because scattered fluorescence emission photons will give rise to background noise rather than contributing to the signal, as can be done with a point-scanning multi-photon system.

A third technique is time-domain lifetime imaging with photon counting. At low-light levels, photon-counting detectors have considerable advantages in that they can virtually eliminate noise contributions from electronic amplifiers or electron multiplier noise in a photomultiplier. Also, photon-counting systems provide quantized pulses for every detected photon, allowing the lifetimes to be measured directly using electronic circuitry. Because of the very high speeds necessary to obtain sub-nanosecond temporal resolution, time-to-voltage converters are usually used to measure the interval between the fluorophore excitation pulse and the time of detection of the emitted fluorescent photon. Such schemes have been successfully used in practical photon-counting lifetime detectors. These schemes are attractive because of their efficient utilization of detected photons. However, they suffer from dynamic range problems that arise out of limited counting speeds. Typically, a time-to-voltage converter together with an associated analog (voltage) to digital converter would have a maximum counting rate of around 1 MHz. Also, with this scheme, only one photon can be measured in the interval between laser pulses. These limitations restrict the use of this technique to low light levels when fairly long exposure times are needed in order to obtain sufficient counts for accurate representation of the decay curve. The comparatively large dead-time of this technique can have more insidious consequences. Immediately after the laser pulse, photons will be emitted at the highest rate and therefore more will be preferentially lost at this time because of the dead-time of the detector. This effect will distort the shape of the decay profile.

SUMMARY OF THE INVENTION

A spectroscopic microscope system in accordance with the invention is particularly suited to multi-photon spectral imaging to analyze the light emanating from a specimen to identify a fluorophore or provide information on the microenvironment of the fluorophore. It is capable of collecting the desired signal in the presence of background noise with a high degree of accuracy where multiple fluorophores are used and in the presence of endogenous fluorophores. By utilizing spectroscopic analysis of the light emitted from the specimen, the microscope system in accordance with the invention avoids the need for complicated and expensive filters to separate fluorophore signals. The invention is particularly well suited to the imaging and analysis of living specimens by maximum utilization of the light emitted from the specimen and passed to a detector. The spectroscopic analysis is carried out rapidly, allowing real-time analysis of living specimens and avoiding high level of fluorophore exposure to the excitation light.

A spectroscopic microscope system in accordance with the present invention utilizes a light source providing a beam of light that includes a chosen long wavelength that is preferably pulsed in short pulses suitable for multi-photon excitation of a fluorophore. A microscope objective lens receives the beam from the light source and focuses it to a narrow point at which a specimen may be positioned. A dichroic mirror is positioned in a first beam path to direct light from the light source to the objective lens and to direct fluorescent light from a specimen passed back through the objective lens to a second beam path away from the source. A spectral dispersive element is positioned in the second beam path to receive the fluorescent light and to spread the light according to its spectral content. A multi-channel detector having multiple detector elements receives the light spread by the spectral dispersive element and provides output signals indicative of photon events detected by each detector element in the array. A preferred detector element is a photomultiplier tube having multiple detector elements positioned in an array, e.g., 32 elements positioned in side-by-side relation. Discriminator electronics may be coupled to receive the output signals from the multiple channel detector that includes comparators for each channel that compare the output signal of the detector to a threshold and provide an output signal when the threshold is exceeded. A counter is connected in each channel to each comparator to count the pulse outputs from the comparator over a selected period of time. In this manner, the photon events counted in each channel indicate the relative spectral content of the light emitted from the specimen with a high degree of accuracy. The system preferably includes a scanning means to scan the beam in a raster fashion over the objective lens. The discriminator electronics incorporates fast comparators and counters that allow collection of the spectroscopic data on a pixel-by-pixel basis as the excitation light beam is scanned over the specimen.

The excitation of fluorophores in the specimen with relatively long wavelength laser light in short pulses suitable for multi-photon excitation will result in the emission of fluorescent photons at shorter wavelengths than the excitation light. The dichroic mirror may be formed to pass wavelengths of light at selected wavelengths, shorter than that of the beam from the source, which include the wavelengths of the multi-photon absorption fluorescent light emitted from a specimen. Preferably, the light source is a pulsed laser providing light in the range of red to near infrared wavelengths.

In a preferred structure of the microscope system, the second beam path includes a multi-mode optical fiber having an entrance end and an exit end and an objective lens in the second beam path positioned to image the exit aperture of the microscope objective lens onto the entrance end of the optical fiber. The exit end of the optical fiber is positioned to direct a cone of light exiting therefrom onto the dispersive element. A preferred dispersive element is a concave curved holographic diffraction grating, which provides a wide aperture that is especially advantageous for analysis of the relatively low intensity level fluorescent light that can be poorly collimated.

The present invention may also carry out simultaneous fluorescence lifetime imaging utilizing the basic spectroscopic microscope system structure. To provide fluorescence lifetime imaging, the discriminator electronics may include multiple channels, each connected to receive the output of a detector element. Each channel includes a comparator comparing the output of the detector to which it is connected to a reference and providing a pulse output signal when the detector signal is above the threshold. A series of counters is connected to each comparator. The laser light source provides short pulses of light at a selected repetition rate. Means are provided operably connected to the laser source to enable the counters in each series of counters in sequence at selected times after initiation of a light pulse from the laser source. The photon counts determined by each counter in a channel after each light pulse from the laser provide an indication of the photon events as a function of time after the light pulse. The means for enabling the counters preferably includes a tapped delay line connected to receive an enable signal corresponding to the initiation of a light pulse from the laser source. The enable signal is propagated along the delay line, each tap of the delay line being connected to the input of an AND gate the other input of which is connected to the comparator; the output of the AND gate at each tap is preferably connected to one of the counters in the series of counters such that the series of counters are enabled to begin counting in sequence at selected progressively delayed periods of time after initiation of the laser light pulse. Preferably, all of the taps of the tapped delay line are reset to a reset level at a selected time after initiation of the laser light pulse and before the next pulse.

Further objects, features and advantages of the invention will be apparent from the following detailed description when taken in conjunction with the accompanying drawings.

DETAILED DESCRIPTION OF THE INVENTION

Figure 1:
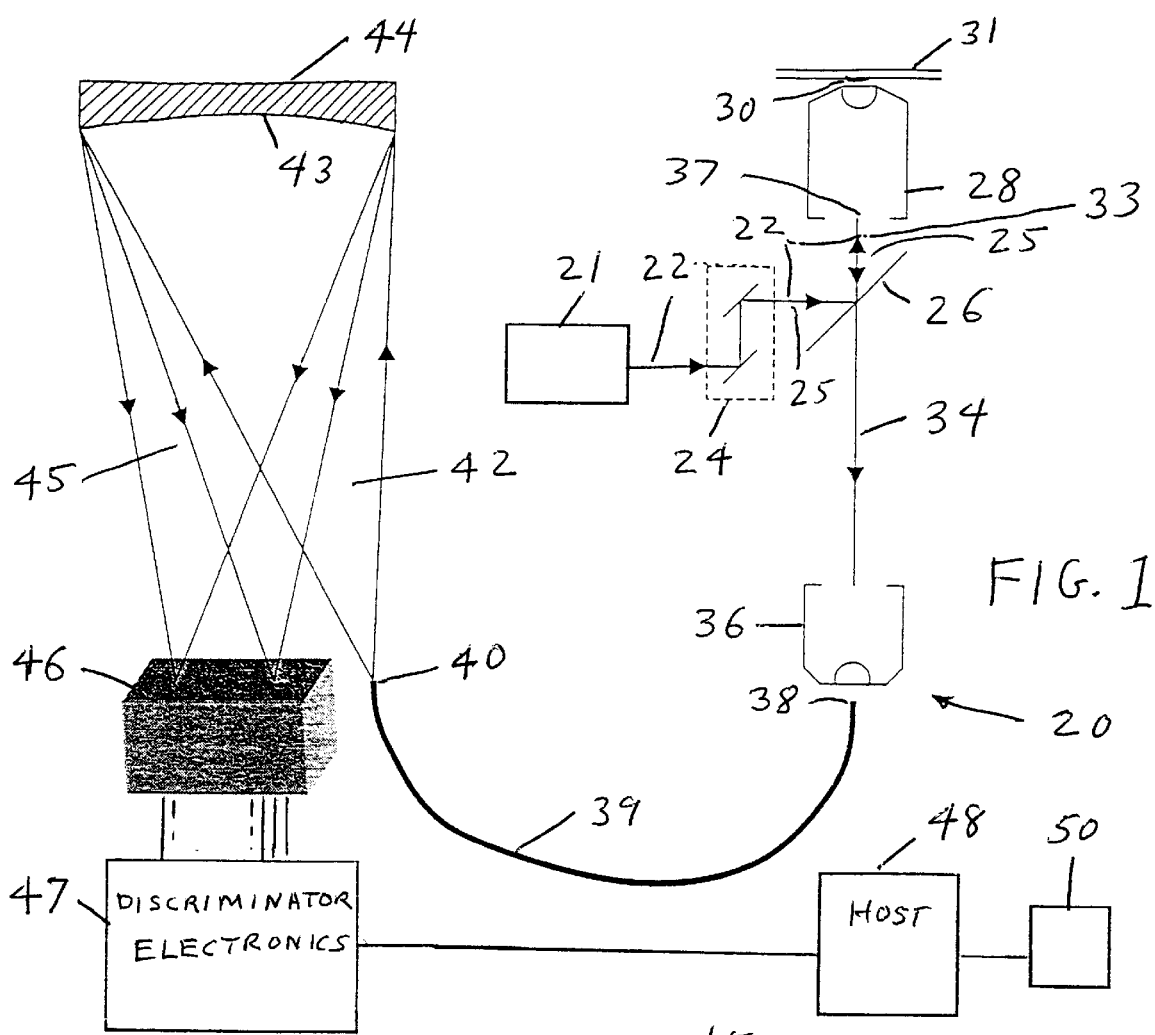
FIG. 1 is a schematic diagram of the optical layout of a spectroscopic microscope system in accordance with the invention.

With reference to the drawings, a two dimensional, photon-sorting spectroscopic microscope system in accordance with the invention is shown generally at 20 in FIG. 1. The spectroscopic microscope system 20 receives excitation light from a source 21, which is typically a pulsed laser providing light in the red or near infrared range. Examples include Nd:YLF lasers and passive modelocked argon-ion primped Ti:sapphire lasers, but any desired source may be utilized. Other examples of lasers are discussed, e.g., in the article by David L.

Wokosin, et al., IEEE J. of Selected Topics in Quantum Electronics, Vol. 2, No. 4, December 1995, pp. 1051–1065. The laser output beam 22 is directed on a first beam path to a scanning system 24 which may include, for example, orthogonally rotatable mirrors which deflect the beam 22 in a raster fashion. Exemplary scanning systems are described in U.S. Pat. No. 5,032,720 to John G. White, entitled Confocal Imaging System, incorporated by reference, but any suitable scanning system may be utilized, a commercial example of which is a BioRad MR-600 Confocal Scanning System. A preferred fast scanning system for multi-photon excitation is described further below. Alternatively, the beam may be fixed and the stage holding the specimen may be moved. The beam exiting the scanning system 24 passes on a first optical path 25 to a dichroic reflecting mirror 26 which deflects the beam on the path 25 to a microscope objective lens 28 of a microscope. The objective lens 28 focuses the incident beam onto a focal spot or waist within a specimen 30 held on a substrate 31 (such as a transparent microscope slide). An exemplary multi-photon excitation source 21 is a Nd:YLF laser providing, for example, a 1 mm diameter beam which is expanded to an 8 mm beam by eyepiece and achromat optics, providing 175 femtosecond (fs) pulses at a selected repetition rate such as 82 MHz, at a wavelength of 1047 nm, and at a laser power of about 800 mw with imaging powers at about 50 mw or less. Appropriate alternative sources, e.g., lasers with longer (or shorter) pulses or continuous beams may also be used, as desired. The microscope optics, including the objective lens 28, may be standard microscope optics (and may each constitute more than one lens element) available from several microscope manufacturers. The scanning system thus effectively scans the beam in a raster fashion onto the objective lens, and the beam focused by the objective lens is scanned in a raster fashion over a specimen.

The light reflected from the specimen 30 and fluorescent light emitted from the specimen that is incident upon the microscope objective 28 is directed back along the beam path 25 to the dichroic reflecting mirror 26. The dichroic mirror 26 is preferably constructed to reflect wavelengths above a selected wavelength, including the wavelength of the light in the beam 22 from the source 21, and to substantially transmit wavelengths below the selected wavelength. The specimen 30 may contain a fluorophore or fluorophores selected to absorb two (or more) photons at the wavelength of the light from the source and to fluorescently emit shorter wavelength photons. Because the fluorescent photons in the beam 33 that are 30 directed back from the specimen through the microscope objective 28 toward the dichroic mirror 26 are at a wavelength below the selected cross-over wavelength of the dichroic mirror, the beam 33 passes through the dichroic mirror 26 and is directed on a second beam path 34 away from the source. The dichroic mirror 26 may be a dichroic mirror design of the type used in, for example, confocal microscopes, that transmit short wavelength light and reflect longer wavelength light (e.g., 850 DCSP available from Chroma Technology, Inc. of Brattleboro, Vt.). Of course, the dichroic mirror may alternatively reflect short wavelengths and transmit long wavelengths with a suitable rearrangement of the beam paths 25 and 34. As used herein, a dichroic mirror includes prisms and other optical components with dichroic reflecting surfaces as well as flat mirrors that may be used to separate light at different wavelengths.

The second beam path 34 preferably includes an objective lens 36 (e.g., a 160 mm tube-length X16 objective) which images the back aperture 37 of the microscope objective 28 onto the entrance end 38 of an optical fiber 39, which has an exit end 40. The optical fiber 39 may comprise, for example, a 1 mm fused silica multi-mode optical fiber (e.g., an Oriel 77514 with a transmission efficiency of 98% and an NA of 0.22). The utilization of the optical fiber 39 allows the spectroscopic components of the system, described further below, to be remotely located from the microscope components. However, it is understood that the utilization of the optical fiber 39 is optional and that the spectroscopic components may be mounted to directly receive the fluorescent light beam on the beam path 34, or the beam path 34 may include other optical components such as mirrors and prisms that direct the beam to the spectroscopic components.

The light emitted from the exit end 40 of the optical fiber cable 39 is a cone of light 42 with, e.g., a solid angle of about 30°. The cone of light 42 is incident upon the surface 43 of a dispersive element 44, such as a diffraction grating. A preferred dispersive element is a concave curved, aberration corrected, holographic grating which uses controlled non-uniformities in the grating spacing to correct for aberrations. Such gratings can have low F-numbers and produce flat-field spectra. An example of a suitable grating is an American Holographic 490.22 grating which has a very high aperture (F2) and is specified for a spectral range of 380–730 nm. Such holographic gratings are sinusoidal and, although this gives a fairly flat efficiency over the spectral range, the efficiency is limited to about 35%. It is also possible to blaze holographic gratings by ion etching, which can increase efficiency up to 55%–85% at the blaze wavelength. By utilizing an optical fiber 39 that has an NA (e.g., 0.22) that matches with the aperture (e.g., F2) of the diffraction grating, the need for coupling optics between the optical fiber and the diffraction grating is avoided.

The light in the cone 42 incident upon the surface 43 of the diffracting element 44 is spread spatially by the element 44 in accordance with the spectra of the light and is directed to a detector 46 which comprises a linear array of detecting elements. A preferred detector array is a multi-anode photomultiplier detector, e.g., a Hamamatsu H7260 formed of a linear array of 32 anodes each 1 mm×7 mm in size. This detector array will provide a spectral discrimination of 10 nm per channel and a total spectral spread of 320 nm when used in conjunction with an American Holographic 490.22 diffraction grating. The anodes in the detector 46 are arranged as a strip of 32 adjacent anodes (i.e., 32 mm×7 mm detector surface area). The detector has one continuous photocathode that is deposited on the inner surface of the detector faceplate. With this type of arrangement, there is no dead space between channels, so that light falling on a transition region between two adjacent anodes causes photoelectrons to be collected by both anodes. The transitional regions are only about 10% of the width of the anode, so that the spatial resolution is kept high without loss of signal in dead spaces between anodes.

It is understood that other suitable detectors may be utilized for the detector 46. For example, avalanche photodiodes (APDs) have high quantum efficiency and are a promising technology for detectors for laser scanning microscopy.

The output signals from the detector 46 are supplied to discriminator electronics 47 which provide photon counting and discrimination, as discussed further below. The discriminator electronics 47 are coupled to a host computer 48 which stores and processes the signals from the discriminator electronics in a standard fashion and which can display the image on a display device 50, such as a video display terminal. The discriminator electronics or the host 48 may also control the scanning of the x-y scanner 24 in a conventional fashion and as described further below.

Figure 2:
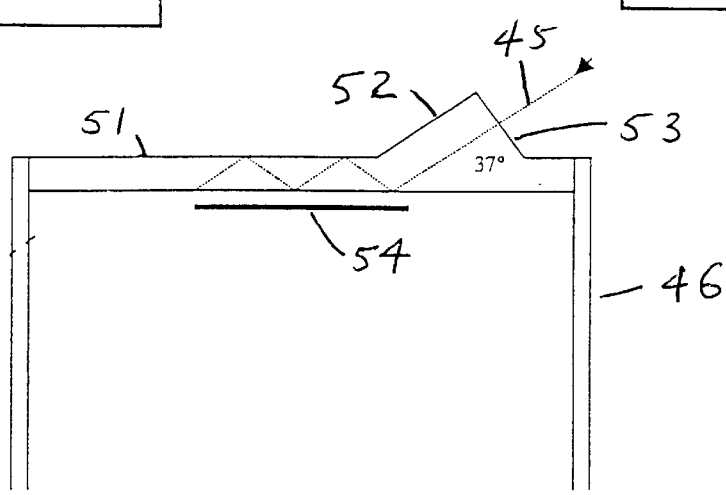
FIG. 2 is a simplified cross-section through a multi-channel photomultiplier tube (PMT) utilizing a roof-top prism on the faceplate of the photomultiplier to enhance the quantum efficiency of the photomultiplier detector.

To increase the quantum efficiency of the photomultiplier tube detector, the faceplate may be utilized as a light guide, as illustrated in FIG. 2. The faceplate 51 of the photomultiplier tube 46 shown in FIG. 2 includes a roof-top prism section 52 with an entrance face 53 which receives the dispersed light 45 from the dispersive element 44. In general, photomultiplier tube photocathodes must be made fairly transparent, causing many photons to pass through without detection. If the photocathode is made thicker to capture more photons, photoelectrons released from within the cathode material will not be able to escape. The coupling prism 52 couples the photons into the faceplate, which acts as a light guide, allowing photons to bounce into the photocathode several times as they migrate within the faceplate, thereby increasing the chances of photoelectron production. In this manner, the quantum efficiency may be increased to in excess of 40% utilizing the enhanced H7260 photomultiplier tube detector. One of the anodes 54 is shown in FIG. 2 along its long axis (i.e., the 7 mm axis). The elongated rooftop prism 52 may be cemented to the faceplate parallel with, but to one side of, the strip of (e.g., 32) anodes. Light directed to the prism 52 is trapped by total internal reflection within the faceplate.

Figure 3:
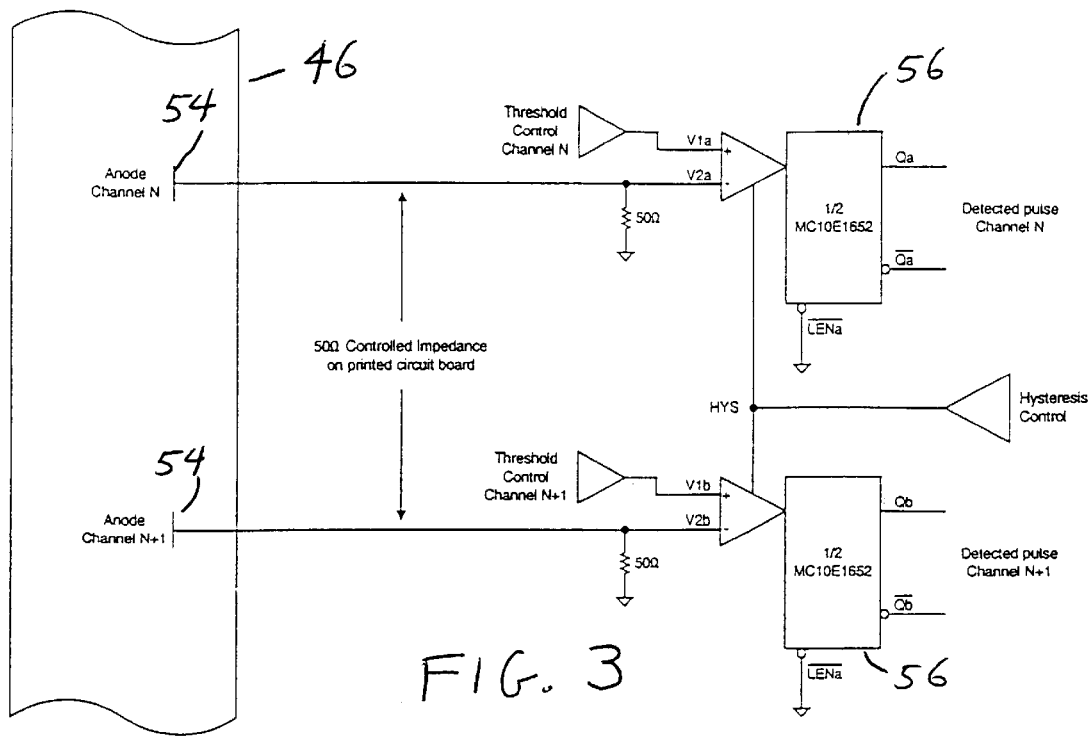
FIG. 3 is a circuit diagram of a portion of the discriminator electronics for the spectroscopic microscope system illustrating the use of high speed comparators to quantize the output of PMT detector channels.

Photon counting may be used in each of the 32 channels to essentially eliminate the effects of noise generated by the electronic circuitry and the electron multiplier noise of the PMT. One potential problem with photon-counting systems is their limited dynamic range imposed by the dead-time associated with a finite maximum counting rate. However, in the present invention, very high counting rates are possible. The H7260 is a very fast device, producing pulses for each detected photon that are around 1 nano-sec. Furthermore, the internal gain of these PMT's is such that the output of each channel can be coupled directly into a high-speed, emitter-coupled logic comparator 56 (Motorola MC10E1652) in the detector electronics 47 as shown in FIG. 3. These comparator devices have externally specifiable values of hysteresis and threshold and directly convert the photon signals from the PMT 46 into quantized pulses of lnsec, obviating the need for wide-band amplifiers on each channel. With this arrangement, stochastic counting speeds of up to 50 MHz can be achieved before the counts lost in the dead-time exceed 10%. All 32 channels are collected in parallel. A typical spectrum will be spread over 10 channels although not equally in each. This parallelism increases the effective counting rate to around 200 MHz for a single spectrum. The pixel dwell time for a typical 512×512 image raster scanned in one second is about 4 $\mu$sec. Therefore, at this scan speed, each spectral element of a pixel can receive a maximum of 200 counts before count pile-up becomes excessive, and the summed intensity from all the spectral elements of a given fluorophore can have a maximum value of 800 counts. In practice, one can rarely achieve 100 counts per pixel when viewing typical in vivo preparations. Indeed, many confocal microscopes have only 8 bit digitization giving a maximum dynamic (contrast) range of 1:256. The dynamic range of the photon counting system of the invention thus is more than adequate for this application.

Figure 4:
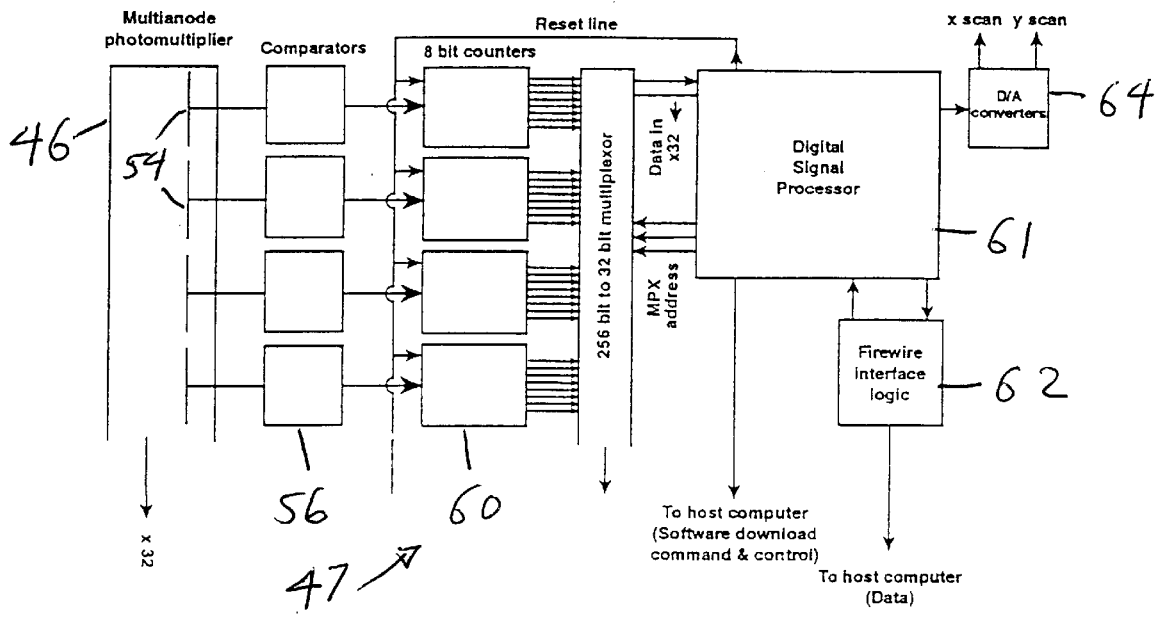
FIG. 4 is a simplified schematic diagram of the discriminator electronics for the spectroscopic microscope system of the invention.

The high speed comparators 56 that are connected to each anode 54 of the 32 channel PMT detector 46 may each be connected to high-speed, 8 bit counters 60 as shown in FIG. 4. The sequence control and readout of the counters is handled by a digital signal processor (DSP) 61. Such devices are high-speed digital processors with architectures that are optimized for repetitious operations on streams of data. They feature large instruction sizes (up to 256 bits) that can perform several operations in parallel. A suitable DSP is the Texas Instruments TMS320C6201 processor. This device is the fastest fixed-point processor currently available (1,600 million operations per second).

The DSP board may be linked to the host computer that runs the laser-scanning control software via a high-speed serial link. An IEEE 1349 interface 62 (also known as "Firewire") may be used to implement this link. This is a high-speed data transmission system (up to 400 Mbps).

In addition to controlling and off-loading data from the 32 channels of 8 bit counters, the DSP may be used to generate the X and Y scan waveforms (via dual digital-to-analog converters (ADCs) 64). These signals are used to drive the gavanometric scanning mirrors in the scanning system 24. In this manner, the data capture and signal processing logic is tightly coupled to the scan-generation logic, thereby facilitating synchronization between these two systems.

The operation and control of the spectral detector and the raster scanning of the spectroscopic microscope system may be split between the DSP (firmware) and the host computer 48 (software). The DSP 61 may handle all the low-level logic such as unloading and resetting the photon-counting scalers and reading out the scan waveforms from downloaded look-up tables to the D/As which drive the galvanometer scanners. In addition, the DSP may be used to bin the 32 channel data into any pre-determined number of spectral bands, each band having a pre-determined spectral width (and individual channels can be included in more than one spectral band). Executing the binning operation in the DSP is fairly simple to implement and minimizes the data transfer rates to the host when less than the full 32 channels is required. New bands may be defined that are simple arithmetic combinations of other bands. Such a band may be the ratio of two other pre-defined bands, for examples, for real-time ratio imaging applications. Alternatively, bands may be subtracted where color difference information is required.

Spectral information may be represented in several ways on an image. The simplest is a real color representation where the 32 channels are mapped onto the three video RGB channels. Pseudocolor representation may also be used where a small range of the spectrum is expanded into an RGB map. This representation may be useful for revealing subtle spectral shifts produced when probes are in different microenvironments within the sample. Full spectral information can be obtained by the user pointing to a particular pixel with a cursor to produce a spectrum in a separate window. Alternatively, the user can draw around an area of interest. This "spatial binning" allows the full 32 channel spectrum of this area to be displayed with improved signal-to-noise ratio.

An overall detection efficiency for photons for the system as described above is around 12%, which is comparable to that of a conventional confocal microscope. The detection optics has a low f-number (2) and is therefore capable of collecting an appreciable amount of non-collimated light from scattered photons. In addition, with the use of the multi-photon collection enhancement as described in Patent Cooperation Treaty Application PCT/US99/01508, publication No. WO 99/37999, published Jul. 29, 1999, and a direct detection configuration, the system of the invention can utilize more than three times the emitted fluorescent photons of a comparable confocal microscope.

By the use of photon counting for signal detection, noise contributions from the electronics and the multiplication noise of the PMT dynode chain are eliminated. The signal-to-noise ratio is simply dependent on the number of detected photons per pixel. If all the spectrometer channels are binned together, the system will behave like a single channel detector that covers the spectral range 390 nm to 710 nm. If the full 32 channel resolution is used, the signal-to-noise ratio of the signals in each channel will obviously be less than the single channel case where all the channels are binned together. However, the spectrum of a typical fluorophore is only spread over around 10 channels. For a typical fluorophore, such as calcium green, about 15% of the total spectral energy is present in a 10 nm wide spectral window positioned at the peak of the emission spectrum. The signal-to-noise ratio of this window is therefore reduced by a factor of around $\sqrt{(100/15)}=2.3$ compared to the signal-to-noise ratio with all the spectral windows binned.

One of the primary advantages of collecting spectral information is that it facilitates the identification of separate spectral components within a fluorescent spectrum. Various software tools may then be utilized for spectral analysis for use in conjunction with the spectral imaging system. By having a library of known and anticipated spectra, it is possible to use computer algorithms to identify the separate fluorophores giving rise to the experimentally obtained spectra. Several techniques are available for doing this. These include the singular value decomposition technique which was developed as a general least-squares fitting algorithm and can be used to identify overlapping spectra. It has been successfully implemented for remote sensing applications. It was found to be somewhat sensitive to noise, but this sensitivity was reduced by iterative techniques. Artificial neural networks may also be used. They are somewhat computationally intensive but have proved powerful in many diverse applications. In the present application, a neural network is "trained" from a library of spectra. In addition, it is trained by common combinations of overlapping spectra (e.g., a FRET pair, or combinations of spectra from commonly used fluorophores). Artificial neural networks have been shown to give good results from noisy specimens, but require a lot of computer time for training. However, once training is completed to satisfactory levels, it does not have to be repeated.

The use of these algorithms in conjunction with the spectral detector of the invention offers the ability to extract better quantitative data from the spectra. This is of crucial importance for studying FRET interactions or for making the best use of ratiometric indicator probes. In addition, the automatic identification of sources of endogenous fluorescence could be particularly useful in some applications.

Figure 5:
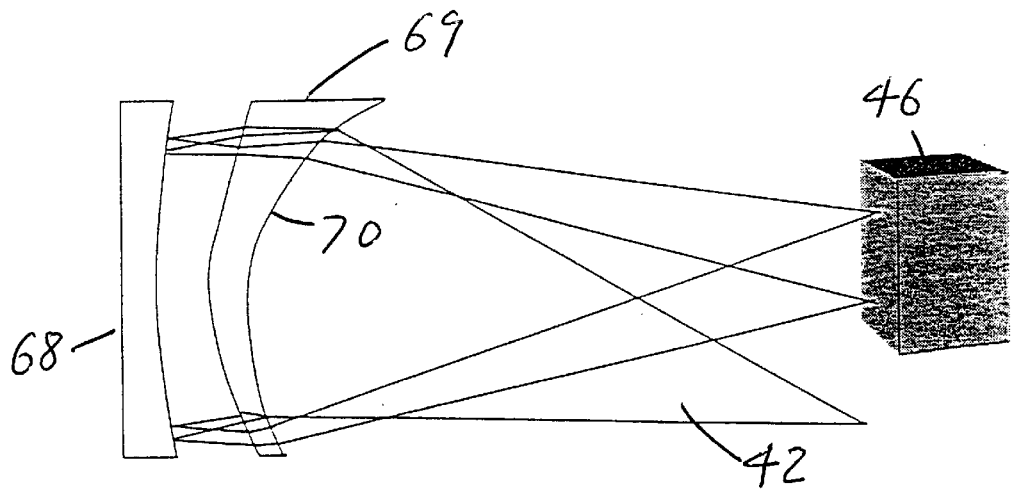
FIG. 5 is a diagram of an alternative dispersive element that may be used in the spectroscopic microscope system of the present invention.

Other suitable dispersive elements 44 may be utilized in the present invention. One example is a refracting spectrometer developed by NASA for a space probe, known as PARISS (Prism and Mirror Imaging Spectroscopy System), which currently is being developed commercially by Light-Form Inc. The system is relatively simple, as shown in FIG. 5, consisting of a concave mirror 68 and a prism 69 with curved surfaces 70. The prism 69 has two spherical surfaces aligned on different axes. It has the advantage of high optical efficiency (about 80%).

The present invention may be embodied in a spectral and lifetime detector for multi-photon microscopy, referred to as a two-dimensional, photon-sorting spectrometer (TDPSS), which overcomes many of the limitations of prior lifetime imaging systems. For utilization in this embodiment, the detector should be as efficient as possible in capturing scattered signal photons. The detector should also be fast so that it can be used in applications such as fast calcium imaging. The system should be capable of sorting individual detected photons in two dimensions according to their spectra and lifetimes. The detector is preferably reconfigurable by software to run in the following modes: simple, single intensity detector; N-channel spectral detector; simple single channel lifetime detector; N-channel lifetime detector; full lifetime and spectral separation (i.e., photons sorted into $N^2$ bins); and the number of channels (N) in the spectral and lifetime axes user-configurable to a maximum determined by the hardware configuration (e.g., N=32 in each axis).

Multi-photon imaging systems generally use ultra-short pulse excitation laser sources (typically 100 femtosec at 100MHz repetition rates) which are about three orders of magnitude shorter than typical fluorescent lifetimes (0.5–20 ns) and therefore make ideal sources for time-domain lifetime imaging. Part of the reason that time-domain methods are not often used for the study of lifetimes is that performance is often limited by dead-time and counting speed, so very high-speed gating circuitry must be employed to get an acceptable dynamic range. However, high-speed logic devices are now available that can switch in 250ps. These factors make time-domain imaging feasible for short lifetimes in multi-photon systems. The present lifetime system, unlike previous systems, does not necessarily require a gated or modulated photodetector. This means that practically no photons are lost, and the system is very efficient (i.e., sensitive). Furthermore, multiple scans of the specimen are not required; a complete spectrum can be acquired in one scan. The basic principal of the TDPSS is that it acts as a photon sorter. Detected photons are sorted according to color (e.g., 32 channels) and lifetime (e.g., 32 channels) and are accumulated into a total of, e.g., 1024 (i.e., 32×32) bins.

Figure 6:
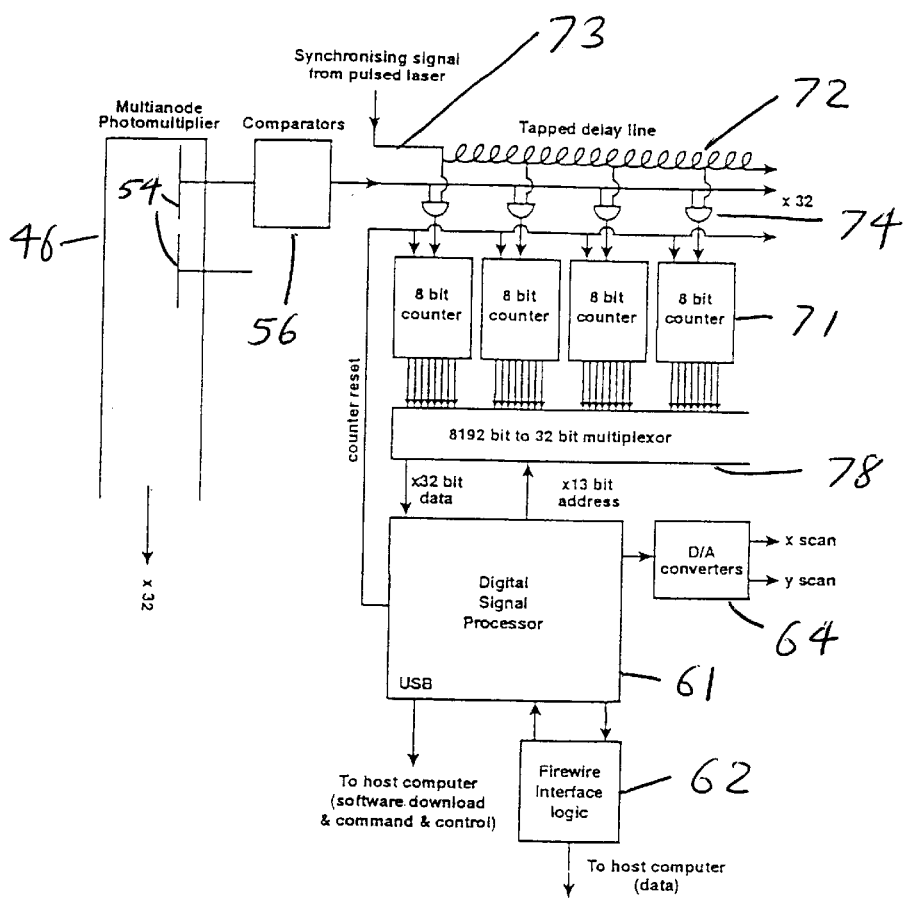
FIG. 6 is a simplified schematic diagram of discriminator electronics for a two-dimensional photon sorting spectroscopic microscope system for fluorescence lifetime imaging in accordance with the invention.

The TDPSS of the present invention preferably utilizes uses the same grating spectrometer optics as the system 20 as shown in FIG. 1. In addition, the same Hamamatsu H7260 32 channel photomultiplier detector 46 may be used with its associated discrimination circuitry of FIG. 4. This device is faster than most conventional photomultipliers, making it ideally suitable for time-resolved measurements. The photomultiplier is used in photon-counting mode, again in the same way as is done in the spectrometer system of FIG. 1. The key difference is that the output from each channel of the photomultiplier is coupled to a series, e.g., 32, 8-bit counters 71, as shown in FIG. 6, instead of just one in the case of the spectral imager. A tapped delay line 72 is used as the timing element for lifetime measurements. The signals from the counters 71 may be supplied to the DSP 61 through a multiplexer (e.g., 8192 bit to 32 bit).

A synchronizing signal is derived from the mode-locked laser 21 and is fed on a line 73 into the tapped, electrical delay-line 72. Various mode-locked lasers may be used which provide such synchronizing pulses (e.g., the Spectrum Physics Tsunami). If a laser is used which does not provide such a signal, the signal can be obtained using a fast photodiode picking up a tap off the main laser beam. The synchronizing signal should be appropriately phase delayed to compensate for the delays in the system electronics. This synchronizing signal is set to logic "1" at the initiation of the laser pulse and drops back to logic "0" just prior to the next pulse. Sequentially delayed versions of this signal are applied to each of the AND gates 74 controlling access of the photomultiplier pulses in each channel to a sequence of 32 counters 71. A counter which has a separate input by which it may be enabled shall be considered an AND gate or the equivalent to an AND gate, and any other desired elements may be used to enable the counters.

Figure 7:
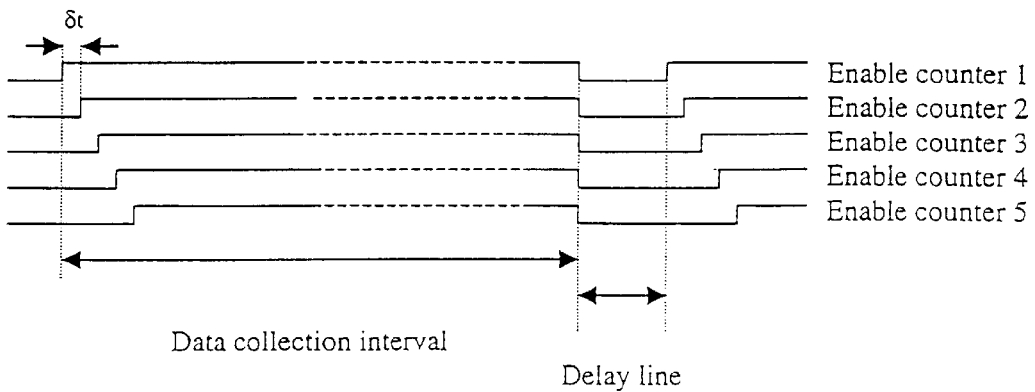
FIG. 7 are timing diagrams illustrating enable times for the first five of 32 counters that accumulate counts of detected photons in the discriminator electronics of FIG. 6.
Figure 8:
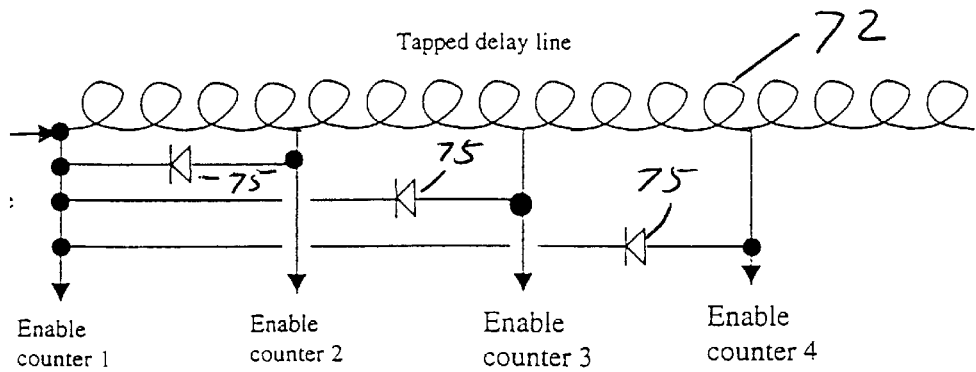
FIG. 8 is a diagram illustrating the delay line circuitry that may be utilized to rapidly reset the delay line at the end of a counting period prior to the arrival of the next laser pulse.

In operation, when the laser delivers a pulse and sets the synchronization line to logic "1", the gate to the first of the counters is enabled and all pulses received thereafter will be counted by the first counter. As the synchronization signal propagates through the delay line, the second counter is enabled after a time determined by the characteristics of the delay line and thereafter counts all the remaining pulses in the sampling interval, as shown in FIG. 7. This process is repeated sequentially until the synchronizing pulse has completely propagated through the delay line and all the counters have been enabled. At the end of a sample period, the synchronization pulse is set to logic "0" causing all of the taps of the delay line to be simultaneously reset through a set of 31 high-speed switching diodes 75 as shown in FIG. 8. This scheme obviates the need to have to wait for the logic "0" level to propagate through the delay line. The count cycle is repeated for every laser pulse in the pixel period. Typically, there would be around 300 laser pulses per pixel period (with an 82 MHz pulse repetition rate laser excitation source and a 4 μsec pixel dwell time).

At the end of the pixel period, the DSP 51 downloads the count values in each counter and then simultaneously resets them all. The DSP 51 determines the number of photons arriving in each time-window by taking the differences in accumulated count between adjacent counters in a single spectral channel. By using this difference method rather than propagation of a count-enabling time window through the counters sequentially, counting ambiguities are avoided which can arise when a photon arrives at the instant the time window is being moved between adjacent counters.

The time axis of the lifetime spectrum is determined by the delay line 72. The delay line device 72 may be constructed as a plug-in module so that various different time scales can be used. This enables both long lifetime luminescent probes (>100ns) as well as prompt fluorescent probes (0.5–10ns) to be measured. A logarithmic time axis may be used if a large dynamic range is required. When studying probes with lifetimes longer than the inter-pulse interval of the laser, the laser will have to be slowed down. This may be achieved by means of a pulse picker that can pick every Nth laser pulse, where N can be 3 or more.

The advantages of the TDPSS system for lifetime imaging include the use of photon counting techniques which thereby give good performance at low light levels. There is very little dead-time with the TDPSS detector. The counting dead-time should be about 2ns and only a few ns will be needed to reset the delay time between pulses. By the use of a delay line as a timing element, multiple counts are possible between laser pulses. The system will be able to count at very high counting rates. The combination of presently available PMT and digital counting circuitry generally is capable of counting at up to 50 MHz stochastically before counts missed because of dead-time reach 10%. A spectrum of a typical fluorophore will be typically spread across 10 parallel counting channels in the spectrometer. For such a fluorophore, the counts in a 10nm wide spectral widow situated at the peak would be about 15% of the counts in the whole spectrum. This means that if all the signals covering the spectrum of a fluorophore are binned together in the DSP, the effective counting rate of the system, for the purposes of lifetime measurements, is increased by a factor of 100/15, i.e., 6.67. This gives an effective stochastic counting rate of 333 MHz, which is around two orders of magnitude better than current-generation photon-counting lifetime spectrometers.

All the coordination and control of the TDPSS is preferably handled by the DSP 61. The DSP can also perform various preprocessing operations on the data in order to minimize the amount of data transferred to the host computer in certain modes of operation. There are four basic modes of operation:

1. Basic grayscale imaging. In this mode of operation, all temporal and spectral information is summed together to give one byte per pixel.
2. N-channel spectral imaging (Ns≦32). The spectral band covered by each channel is pre-defined. The first temporal channel contains the accumulated photon count and so only this one channel must be read out by the DSP.
3. N-channel lifetime imaging (Nt≦32). The mapping of the basic 32 temporal channels into the N user channels is pre-defined. For example, N may be set to two with the first two basic temporal channels accumulated into N1 and the remaining 30 basic temporal channels accumulated into N2. All spectral channels are accumulated together.
4. Two dimensional detection using Ns pre-defined spectral channels and Nt pre-defined temporal channels. This is the full two-dimensional photon sorting mode of the detector. There will be Ns×Nt bytes of information per pixel, each byte corresponding to a count of accumulated photons.

The DSP 61 may be selected to have a 32 bit input/output bus and a basic cycle time of 5ns. The DSP 61 does not have to participate in the photon counting process but has to download the counts in each of the counters at each pixel period. Multiplexers 78 are used so that all the counters 71 may be addressed by means of 32 separate read operations. The logic is preferably set up such that individual counters 71 are reset only after being addressed and their contents downloaded by the DSP 61. This ensures that there is minimal detector latency as the counters are read out.

Data downloading from the DSP 61 to the host computer is preferably mediated by a Firewire interface 62 in the same way as described for the spectral imaging system 20. To the host computer, the TDPSS appears the same as the spectral imager but with extra functionality.

Once in the host computer, exponential curve fitting routines may be used to deduce lifetimes from the data. In practice, a user may first image a field spectrally and identify a region of interest and a spectral window that best displays this region. Then, the TDPSS may be set up into lifetime mode with spectral binning over the required region of the spectrum. Lifetimes can be computed for each pixel and displayed as pseudocolor. In order to decrease noise, the data may be spatially averaged using a n×n smoothing convolution kernel.

Most confocal and multi-photon imaging systems use servocontrolled, galvanometer driven mirrors as scanning elements for XY scanners such as the scanning system 24 of FIG. 1. These devices can provide excellent linearity and are easy to drive electronically. However, they are limited in scanning speed to a maximum of around 700 lines per second. Acousto-Optical (AO) deflection systems have no mechanical inertia and can readily scan at video rates; however, such devices are by nature dispersive and so cannot be used to de-scan a broad band emission in a confocal microscope. Multi-photon imaging systems do not require that the emission path be de-scanned, making AO devices attractive for multi-photon systems subject to some limitations. The AO elements may produce a high degree of chirp in femtosecond laser pulses that can be difficult to remove by compensation, with pulse broadening at the sample and consequent loss of efficiency. In addition, femtosecond pulses are significantly chromatically broadened. Because an AO deflector is essentially a variably spaced diffraction grating, this can lead to different color components being deflected at different angles. Alternatively, rotating polygon mirrors could be used for high speed scanning, potentially several thousand lines per second, but their fixed geometry precludes any optical zooming capability.

Figure 9:
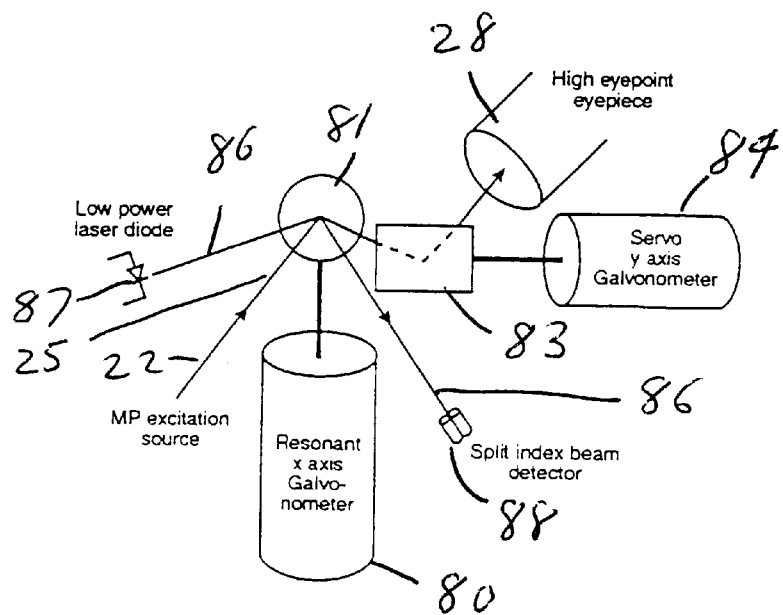
FIG. 9 is a simplified diagram of a beam scanning system having a rapid resonant scanner along one axis that may be utilized in the present invention.
Figure 10:
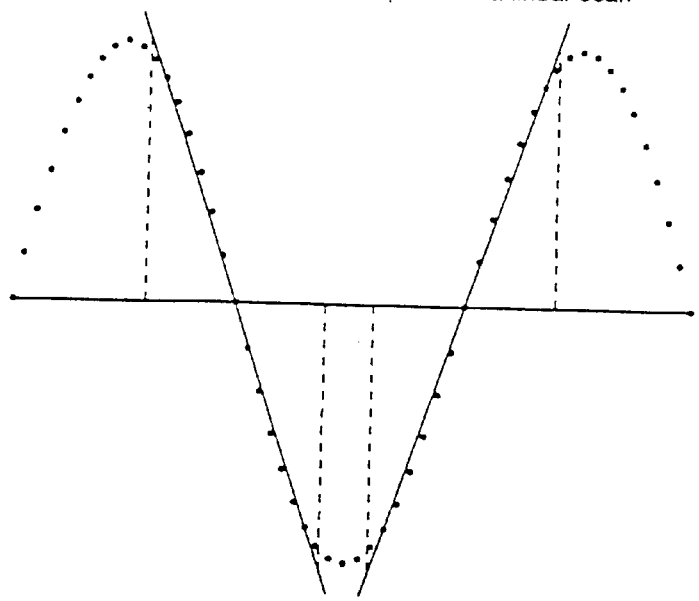
FIG. 10 is a diagram illustrating the portion of the scanning cycle of the resonant scanner that may be used in the scanning system.

A fast scanning system that may be utilized for the scanner 24 for multi-photon scanning is illustrated in FIG. 9 and includes a resonance scanning device 80 having a mirror 81 driven in oscillation, typically at rates up to about 8,000 Hz, which can be used as the X-axis scanner. The Y-axis scan is provided by a conventional mirror 83 driven by a galvanometer 84. The excitation beam 22 is directed along the beam path 25, reflecting off of the two mirrors 81 and 83 before being directed to the objective lens 28 (via the dichroic mirror 26 or other suitable elements not shown in FIG. 10 for simplicity). An example of a suitable commercial resonant galvanometer scanner is the CR Scanner from General Scanning. Such devices are simple, compact and reliable, but have certain disadvantages when used in microscope scanning systems. A first disadvantage is that the devices must be allowed to run free, and thus an accurate indexing system is required to synchronize the scan-control electronics. A second problem is that the scan is sinusoidal, and must be bi-directional in order to obtain a duty cycle greater than 50%. In accordance with the invention, these problems may be resolved by controlling the scanners 80 and 84 by the high speed DSP 61 to perform high accuracy indexing and to linearize the X scan by using variable pixel sample times. Bi-directional scanning may be used in only the two regions of the sine wave that deviate from a linear ramp by less than 5%, as indicated by the straight lines on the drawing of the sinusoidal scan in FIG. 10. This provides a 70% duty cycle which is about the same as that obtained in the current generation of servo-galvanometer scanners running at 500 lines per second. To provide indexing of the galvanometer, an auxiliary beam 86 is provided from a low power light source (e.g., laser diode) 87, preferably operating at infrared wave lengths, with the beam 86 being directed to and reflected from the resonant galvanometer mirror 81. The reflected beam 86 is directed to a split index beam detector 88. The detector 88 is positioned close to the zero crossing point of the scan, where scan velocity is at its greatest. The output of the beam detector 88 is provided to the DSP 61. The DSP utilizes the index signal from the detector to lock a digitally synthesized clock by means of a phase-locked loop. Such a system is robust and stable, and low level jitter on the indexing signal can be smoothed out by an appropriate choice of time constant in the phase-locked loop. The DSP utilizes this clock, in conjunction with pre-computed lookup tables, to generate the timing intervals used for sampling data. In this way, the +/−5% non-linearity of the 70% of the sinusoidal scan that is used can be corrected by varying the data sample intervals. This procedure capitalizes on the high processing speeds of the DSP. Further, the oscillating galvanometer mirror 81 is effectively a weight oscillating on a spring, and behaves in a smooth and predictable way (analogous to a pendulum clock). The DSP synthesized pixel clock has low susceptibility to indexing jitter and can be used at varying scan amplitudes, allowing images to be optically zoomed.

Commercial DSPs, such as the Texas Instrument TMS 320C6201DSP, can operate at 1600 million instructions per second and can be utilized to operate the scanning system together with either of the detectors. It is preferable to control the detectors and scanning system by one high speed processing unit to provide simplicity and economy of design, and particularly to tightly coordinate the detector sampling with the scan generation logic. Further, the same DSP is preferably utilized to set up the parameters of the detectors (e.g., channel number and spectral width) and the scanner (e.g., raster aspect ratio and zoom value). Under control of the DSP, typical specifications for the high speed scanner include a bi-directional scan-line rate of 6,000 lines per second. This rate comes close to the maximum rate at which the present Fire-wire interface can transfer data to the host computer when the detector is configured to produce 32 bytes of data per pixel in a 256×256 raster. The system thus is able to capture 32 channel images at a framing rate of 23 frames/second for a 256×256 raster. When used with the two dimensional photon sorting detector system of FIG. 7, the 32 channels can be any mix of spectral or lifetime channels not to exceed a total of 32. The user may then specify the number of lines per frame, the number of pixels per line and the overall zoom value. At the highest resolution (1024× 1024) the framing rate will be around 6 frames per second. Preferably, all of the controlling software for the high speed scanning system is incorporated in the DSP 61 and is integrated with the software controlling the spectral detectors or the two dimensional photon sorting detectors. The controlling software in the host computer 48 can be similar to that used for the conventional slower, all servo scanner systems.

It is understood that the invention is not limited to the particular embodiments set forth herein as illustrative, but embraces all such forms thereof as come within the scope of the following claims.

What is claimed is:

1. A spectroscopic microscope system comprising:
    (a) a light source providing a source beam of light that includes a chosen wavelength;
    (b) a microscope objective lens receiving the beam from the light source, the objective lens focussing the beam to a narrow point at which a specimen may be positioned;
    (c) a dichroic mirror positioned in a first beam path to direct light from the light source to the objective lens and to direct fluorescent light from a specimen passed back through the objective lens on a second beam path away from the source;
    (d) a spectral dispersive element comprising a concave curved holographic diffraction grating positioned in the second beam path to receive the fluorescent light and to spread the light according to its spectral content; and
    (e) a multiple channel detector having multiple detector elements positioned in an array to receive the light spread by the spectral dispersive element and to provide output signals indicative of photon events detected by each detector element in the array.

2. The spectroscopic microscope system of claim 1 including discriminator electronics connected to receive the output signals from the multiple channel detector and including comparators for each channel that compare the output signal of the detector to a threshold and provide an output signal when the threshold is exceeded, and a counter connected in each channel to each comparator to count the pulse outputs from the comparator over a selected period of time.

3. The spectroscopic microscope system of claim 1 including a scanning means receiving the beam from the source for scanning the beam in a raster fashion onto the objective lens.

4. The spectroscopic microscope system of claim 3 wherein the dichroic mirror is positioned to receive the beam from the scanning means and to reflect the beam at the wavelength of the light from the source onto the objective lens, the dichroic mirror formed to pass wavelengths of light therethrough at selected wavelengths shorter than the wavelength of the beam from the source which include wavelengths of fluorescent light emitted from a specimen due to multi-photon absorption.

5. The spectroscopic microscope system of claim 1 wherein the light source is a pulsed laser providing light in the range of red to near-infrared wavelengths.

6. The spectroscopic microscope system of claim 1 wherein the second beam path includes a multi-mode optical fiber having an entrance end and an exit end, and an objective lens in the second beam path positioned to image an exit aperture of the microscope objective lens onto the entrance end of the optical fiber, the exit end of the optical fiber positioned to direct a cone of light exiting therefrom onto the holographic grating dispersive element.

7. The spectroscopic microscope system of claim 1 wherein the multiple channel detector is a photomultiplier tube having multiple photomultiplier tube detector elements positioned in an array.

8. The spectroscopic microscope system of claim 1 including discriminator electronics connected to receive the output signals from the multiple channel detector wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, wherein the laser source is a pulsed source providing short pulses of light at a selected repetition rate, and including means operably connected to the laser source for enabling the counters in each series of counters in sequence at selected times after initiation of a light pulse from the laser source.

9. A spectroscopic microscope system comprising:
   (a) a light source providing a source beam of light that includes a chosen wavelength;
   (b) a microscope objective lens receiving the beam from the light source, the objective lens focussing the beam to a narrow point at which a specimen may be positioned;
   (c) a dichroic mirror positioned in a first beam path to direct light from the light source to the objective lens and to direct fluorescent light from a specimen passed back through the objective lens on a second beam path away from the source;
   (d) a spectral dispersive element comprising a concave curved holographic diffraction grating positioned in the second beam path to receive the fluorescent light and to spread the light according to its spectral content;
   (e) a multiple channel detector having multiple detector elements positioned in an array to receive the light spread by the spectral dispersive element and to provide output signals indicative of photon events detected by each detector element in the array; and
   (f) discriminator electronics connected to receive the output signals from the multiple channel detector wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator;
      wherein the laser source is a pulsed source providing short pulses of light at a selected repetition rate, and including means operably connected to the laser source for enabling the counters in each series of counters in sequence at selected times after initiation of a light pulse from the laser source; and
      wherein the means for enabling the counters includes a tapped delay line connected to receive an enable signal corresponding to the initiation of a light pulse from the laser source and propagating the enable signal along the delay line, each tap of the tapped delay line connected to an input of an AND gate the other input of which is connected to the comparator and the output of which is connected to one of the counters in the series of counters such that the series of counters are enabled to begin counting in sequence at selected periods of time after the initiation of the laser light pulse.

10. The spectroscopic microscope system of claim 9 further including means for simultaneously resetting all of the taps of the tapped delay line to a reset level a selected period of time after initiation of the laser light pulse.

11. A two dimensional photon sorting spectrometer system comprising:
   (a) a laser source providing a source beam of light in short pulses at a selected repetition rate;
   (b) a microscope objective lens receiving the beam from the light source, the objective lens focussing the beam to a narrow point at which a specimen may be positioned;
   (c) optical elements positioned in a first beam path to direct light from the light source to the objective lens and to direct fluorescent light from a specimen passed back through the objective lens on a second beam path away from the source;
   (d) a spectral dispersive element positioned in the second beam path to receive the fluorescent light from the specimen and to spread the light according to its spectral content;
   (e) a multiple channel array detector having multiple detector elements positioned to receive the light spread by the spectral dispersive element and to provide output signals indicative of photon events detected by each detector element in the array; and
   (f) discriminator electronics connected to receive the output signals from the multiple channel array detector, wherein the discriminator electronics includes multiple channels, each channel connected to receive the output of a detector element, each channel including a comparator comparing the output of the detector to which it is connected to a and providing a pulse output signal when the detector signal is above the threshold reference and a series of counters each connected to the comparator, and including means operably connected to the laser source for enabling the counters in each series of counters in sequence at selected times after initiation of a light pulse from the laser source.

12. The spectrometer of claim 11 including a scanning means receiving the beam from the laser source for scanning the beam in a raster fashion onto the objective lens.

13. A two dimensional photon sorting spectrometer system comprising:
   (a) a laser source providing a source beam of light in short pulses at a selected repetition rate;
   (b) a microscope objective lens receiving the beam from the light source, the objective lens focussing the beam to a narrow point at which a specimen may be positioned;
   (c) optical elements positioned in a first beam path to direct light from the light source to the objective lens and to direct fluorescent light from a specimen passed back through the objective lens on a second beam path away from the source;
   (d) a spectral dispersive element positioned in the second beam path to receive the fluorescent light from the specimen and to spread the light according to its spectral content;
   (e) a multiple channel array detector having multiple detector elements positioned to receive the light spread by the spectral dispersive element and to provide output signals indicative of photon events detected by each detector element in the array; and (f) discriminator electronics connected to receive the output signals from the multiple channel array detector, wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, and including means operably connected to the laser source for enabling the counters in each series of counters in sequence at selected times after initiation of a light pulse from the laser source;

wherein the means for enabling the counters includes a tapped delay line connected to receive an enable signal corresponding to the initiation of a light pulse from the laser source and propagating the enable signal along the delay line, each tap of the tapped delay line connected to an input of an AND gate the other input of which is connected to the comparator and the output of which is connected to one of the counters in the series of counters such that the series of counters are enabled to begin counting in sequence at selected periods of time after the initiation of the laser light pulse.

14. The spectrometer of claim 13 further including means for simultaneously resetting all of the taps of the tapped delay line to a reset level a selected period of time after initiation of the laser light pulse.

15. The spectrometer of claim 11 including a scanning means receiving the beam from the laser source for scanning the beam in a raster fashion onto the objective lens, wherein the optical elements include a dichroic mirror positioned to receive the beam from the scanning means and to reflect the beam at the wavelength of the light from the laser source onto the objective lens, the dichroic mirror formed to pass wavelengths of light therethrough at selected wavelengths shorter than the wavelength of the beam from the laser source which include wavelengths of fluorescent light emitted from a specimen due to multi-photon absorption.

16. The spectrometer of claim 15 wherein the laser source provides light in the range of red to near-infrared wavelengths.

17. The spectrometer of claim 11 wherein the optical elements in the second beam path include a multi-mode optical fiber having an entrance end and an exit end, and an objective lens in the second beam path positioned to image an exit aperture of the microscope objective lens onto the entrance end of the optical fiber, the exit end of the optical fiber positioned to direct a cone of light exiting therefrom onto the dispersive element.

18. The spectrometer of claim 17 wherein the dispersive element is a concave curved holographic grating.

19. The spectrometer of claim 11 wherein the detector is a photomultiplier tube having multiple detector elements positioned in an array.

20. A spectrometer detector system for use with a laser source for illuminating a specimen wherein the laser source is a pulsed source providing short pulses of light at a selected repetition rate, comprising:

(a) a multiple channel detector having multiple detector elements that can receive the light spread by a spectral dispersive element to provide output signals indicative of photon events detected by each detector element in the array; and (b) discriminator electronics connected to receive the output signals from the multiple channel array detector, wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, and including a tapped delay line having multiple taps which is connected to receive an enable signal corresponding to the initiation of a light pulse from the laser source and propagating the enable signal along the delay line, the taps of the tapped delay line and the output of the comparator connected to the counters in the series of counters such that the series of counters are enabled to begin counting in sequence at selected periods of time after the initiation of the laser light pulse.

21. The spectrometer detector system of claim 20 further including means for simultaneously resetting all of the taps of the tapped delay to a reset level a selected period of time after initiation of the laser light pulse.

22. The spectrometer detector system of claim 20 including a spectral dispersive element positioned in a beam path to receive a beam of light and to spread the light according to its spectral content, wherein the beam path includes a multi-mode optical fiber having an entrance end and an exit end, and an objective lens in the beam path positioned to image light in the beam path onto the entrance end of the optical fiber, the exit end of the optical fiber positioned to direct a cone of light exiting therefrom onto the dispersive element.

23. The spectrometer detector system of claim 22 wherein the dispersive element is a concave curved holographic grating.

24. A spectrometer detector system for use with a laser source for illuminating a specimen wherein the laser source is a pulsed source providing short pulses of light at a selected repetition rate, comprising:

(a) a multiple channel detector having multiple detector elements that can receive the light spread by a spectral dispersive element to provide output signals indicative of photon events detected by each detector element in the array; and (b) discriminator electronics connected to receive the output signals from the multiple channel array detector, wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, and including a tapped delay line having multiple taps which is connected to receive an enable signal corresponding to the initiation of a light pulse from the laser source and propagating the enable signal along the delay line, the taps of the tapped delay line and the output of the comparator connected to the counters in the series of counters such that the series of counters are enabled to begin counting in sequence at selected periods of time after the initiation of the laser light pulse;

the detector has 32 detector elements and the discriminator electronics has 32 channels, each channel connected to receive the output of a detector element.

25. A spectrometer detector system for use with a laser source for illuminating a specimen wherein the laser source is a pulsed source providing short pulses of light at a selected repetition rate, comprising:
(a) a multiple channel detector having multiple detector elements that can receive the light spread by a spectral dispersive element to provide output signals indicative of photon events detected by each detector element in the array; and
(b) discriminator electronics connected to receive the output signals from the multiple channel array detector, wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, and including a tapped delay line having multiple taps which is connected to receive an enable signal corresponding to the initiation of a light pulse from the laser source and propagating the enable signal along the delay line, the taps of the tapped delay line and the output of the comparator connected to the counters in the series of counters such that the series of counters are enabled to begin counting in sequence at selected periods of time after the initiation of the laser light pulse;
wherein there are 32 counters in the series of counters in each channel.

26. The spectrometer detector of claim 20 wherein the detector is a photomultiplier tube having multiple detector elements positioned in an array.

27. A spectrometer detector system for use with a laser source for illuminating a specimen wherein the laser source is a pulsed source providing short pulses of light at a selected repetition rate, comprising:
(a) a multiple channel detector having multiple detector elements that can receive the light spread by a spectral dispersive element to provide output signals indicative of photon events detected by each detector element in the array;
(b) discriminator electronics connected to receive the output signals from the multiple channel array detector, wherein the discriminator electronics includes multiple channels, each channel connected to receive the output of a detector element, each channel including a comparator comparing the output of the detector to which it is connected to a reference and providing a pulse output signal when the detector signal is above the threshold and a series of counters each connected to the comparator, and including a tapped delay line having multiple taps which is connected to receive an enable signal corresponding to the initiation of a light pulse from the laser source and propagating the enable signal along the delay line, the taps of the tapped delay line and the output of the comparator connected to the counters in the series of counters such that the series of counters are enabled to begin counting in sequence at selected periods of time after the initiation of the laser light pulse; and
(c) a series of AND gates the outputs of which are connected each to one of the counters, the inputs of each AND gate connected to one of the taps of the delay line and the output of the comparator.

28. A method for analyzing fluorescence in a specimen comprising:
(a) providing a source beam of light that includes a chosen wavelength, the light in the beam being provided in pulses, and directing the beam to a microscope objective lens that focuses the beam to a narrow point in the specimen;
(b) receiving the fluorescent light that is emitted from the specimen and passed back through the objective lens and separating the fluorescent light from the source beam light;
(c) spatially dispersing the fluorescent light in accordance with the wavelengths of the fluorescent light and detecting the dispersed fluorescent light with multiple detector elements each of which detects fluorescent light in a different wavelength range, each detector element providing an output signal which is indicative of photon events detected by the detector element; and
(d) counting the photon events detected by each detector element as a function of time over a selected period of time following a pulse of light in the source beam whereby fluorescence lifetime information can be obtained concurrently with spectral information.

29. The method of claim 28 further including scanning the source beam in a raster fashion onto the objective lens to scan the beam focussed by the objective lens over the specimen in a raster fashion.

30. The method of claim 28 wherein the step of spectrally dispersing the fluorescent light comprises directing the fluorescent light to a spectrally dispersive concave holographic grating which disperses the light spatially to the detectors arranged in an array.

31. The method of claim 28 wherein the step of counting the photon events as a function of time in each channel comprises comparing the output signal from the detector element for the channel to a reference and providing a pulse output signal when the detector signal exceeds the reference to provide a series of pulses corresponding to the photon events detected by the detector element, and further including counting the pulses in the series corresponding to photon events in a series of counters connected to receive the series of pulses, each counter in the series beginning counting at a different period of time after the pulse of light in the source beam is incident upon the specimen, and ending the count in each counter a selected period of time after the pulse of light in the source beam is incident upon the specimen, whereby the value of the counts in the counters is indicative of the photon events as a function of time after the light pulse in the source beam as a function of time for the range of wavelengths detected by the detector for the spectral channel.

32. A method for analyzing fluorescence in a specimen comprising:
(2) providing a source beam of light that includes a chosen wavelength, the light in the beam being provided in pulses, and directing the beam to a microscope objective lens that focuses the beam to a narrow point in the specimen;
(b) receiving the fluorescent light that is emitted from the specimen and passed back through the objective lens and separating the fluorescent light from the source beam light;
(c) spatially dispersing the fluorescent light in accordance with the wavelengths of the fluorescent light and detecting the dispersed fluorescent light with multiple detector elements each of which detects fluorescent light in a different wavelength range, each detector element providing an output signal which is indicative of photon events detected by the detector element; and (d) counting the photon events detected by each detector element as a function of time over a selected period of time following a pulse of light in the source beam whereby fluorescence lifetime information can be obtained concurrently with spectral information;

wherein the step of counting the photon events as a function of time in each channel comprises comparing the output signal from the detector element for the channel to a reference and providing a pulse output signal when the detector signal exceeds the reference to provide a series of pulses corresponding to the photon events detected by the detector element, and further including counting the pulses in the series corresponding to photon events in a series of counters connected to receive the series of pulses, each counter in the series beginning counting at a different period of time after the pulse of light in the source beam is incident upon the specimen, and ending the count in each counter a selected period of time after the rulse of light in the source beam is incident upon the specimen, whereby the value of the counts in the counters is indicative of the photon events as a function of time after the light pulse in the source beam as a function of time for the range of wavelengths detected by the detector for the spectral channel; and wherein there are 32 or more counters in each spectral channel.

33. The method of claim 32 wherein there are 32 detector elements and 32 detector channels.

34. The method of claim 31 wherein each counter is enabled a different delayed period of time after the pulse of light is incident upon the specimen by providing a pulse signal corresponding to the time of the pulse of light in the source beam to a tapped delay line, and providing the output signal at each of the taps of the tapped delay line as an enable signal to each of the counters to enable the counters to begin counting in sequence as the pulse propagates down the delay line and reaches of the taps of the delay line in sequence.

35. The method of claim 31 including the further step of simultaneously resetting counters a selected period of time after the pulse of light in the source beam and before the next pulse of light in the source beam.

* * * * *

UNITED STATES PATENT AND TRADEMARK OFFICE
CERTIFICATE OF CORRECTION

PATENT NO. : 6,687,000 B1
DATED : February 3, 2004
INVENTOR(S) : John G. White

It is certified that error appears in the above-identified patent and that said Letters Patent is hereby corrected as shown below:

Column 1,
Line 2, delete the phrase "support warded by" and replace it with -- support awarded by --.

Column 8,
Line 61, delete "MR-600" and replace it with -- MRC-600 --.

Column 11,
Line 25, delete "Insec," and replace it with -- 1nsec --.

Column 20,
Line 35, delete the phrase "connected to a and providing" and replace it with -- connected to a reference and providing --.

Column 22,
Line 62, add the word -- wherein -- before the phrase "the detector has 32 detector elements" to read -- wherein the detector has 32 detector elements --.

Signed and Sealed this

Twelfth Day of October, 2004

JON W. DUDAS
*Director of the United States Patent and Trademark Office*